(12) United States Patent
Arginteanu (10) Patent No.: US 9,114,020 B2
(45) Date of Patent: Aug. 25, 2015

(54) DEVICE AND METHOD FOR SPINAL FUSION SURGERY

(76) Inventor: Marc Arginteanu, Cresskill, NJ (US)

( * ) Notice: Subject to any disclaimer, the term of this patent is extended or adjusted under 35 U.S.C. 154(b) by 298 days.

(21) Appl. No.: 13/446,476

(22) Filed: Apr. 13, 2012

(65) Prior Publication Data

US 2013/0274881 A1  Oct. 17, 2013

(51) Int. Cl.
*A61F 2/44* (2006.01)
*A61F 2/46* (2006.01)
*A61F 2/30* (2006.01)

(52) U.S. Cl.
CPC ............. *A61F 2/442* (2013.01); *A61F 2/447* (2013.01); *A61F 2/4611* (2013.01); *A61F 2002/30387* (2013.01); *A61F 2002/30393* (2013.01); *A61F 2002/30401* (2013.01); *A61F 2002/30484* (2013.01); *A61F 2002/30509* (2013.01); *A61F 2002/30579* (2013.01); *A61F 2002/30598* (2013.01); *A61F 2002/30785* (2013.01); *A61F 2002/30789* (2013.01); *A61F 2002/30828* (2013.01); *A61F 2002/4475* (2013.01); *A61F 2002/4628* (2013.01)

(58) Field of Classification Search
CPC ............. A61F 2/447; A61F 2002/30845
USPC .................................. 623/17.16, 17.11
See application file for complete search history.

(56) References Cited

U.S. PATENT DOCUMENTS

| | | | | |
|---|---|---|---|---|
| 4,599,086 A | * | 7/1986 | Doty | 606/86 A |
| 4,892,545 A | * | 1/1990 | Day et al. | 623/17.11 |
| 5,062,850 A | * | 11/1991 | MacMillan et al. | 623/17.11 |
| 5,236,460 A | * | 8/1993 | Barber | 623/17.15 |
| 5,443,515 A | * | 8/1995 | Cohen et al. | 623/17.16 |
| 5,800,547 A | * | 9/1998 | Schafer et al. | 623/17.16 |
| 5,800,550 A | * | 9/1998 | Sertich | 623/17.16 |
| 5,810,820 A | * | 9/1998 | Santori et al. | 606/63 |
| 5,849,004 A | * | 12/1998 | Bramlet | 606/232 |
| 6,179,873 B1 | * | 1/2001 | Zientek | 623/17.11 |
| 6,770,096 B2 | | 8/2004 | Bolger et al. | |
| 7,594,932 B2 | | 9/2009 | Aferzon et al. | |
| 7,618,454 B2 | | 11/2009 | Bentley et al. | |
| 7,704,279 B2 | * | 4/2010 | Moskowitz et al. | 623/17.11 |
| 7,918,875 B2 | * | 4/2011 | Lins et al. | 606/248 |
| 8,313,528 B1 | * | 11/2012 | Wensel | 623/17.11 |
| 8,540,769 B2 | * | 9/2013 | Janowski et al. | 623/17.11 |
| 8,617,245 B2 | * | 12/2013 | Brett | 623/17.16 |
| 2005/0049590 A1 | * | 3/2005 | Alleyne et al. | 606/61 |
| 2006/0095136 A1 | * | 5/2006 | McLuen | 623/23.47 |
| 2011/0040334 A1 | | 2/2011 | Kaes et al. | |
| 2013/0261747 A1 | * | 10/2013 | Geisert | 623/17.16 |

FOREIGN PATENT DOCUMENTS

FR       2992166       *   6/2012

* cited by examiner

*Primary Examiner* — David Bates
(74) *Attorney, Agent, or Firm* — Donald J. Ranft; Kristen A. Mogavero; Collen IP (57) ABSTRACT

A spinal fixation and fusion device and method for its use. The device includes a minimum of one stabilization member integral within at least one wall of the device. The stabilization member is typically a pin which when the device is in a final position between the vertebrae stabilization member which is typically a pin is inserted into vertebrae. Specially designed pliers like device can be used for insertion of the pins. A locking mechanism provides a means for securing the pin in place after its insertion.

4 Claims, 12 Drawing Sheets

DEVICE AND METHOD FOR SPINAL FUSION SURGERY

BACKGROUND

Several surgical approaches have been used to implant devices used for spinal fusion. Anterior approaches to cervical, lumbar and thoracic spine are well accepted methods. In certain situations it is beneficial to access the lumbar spine via a direct lateral approach or a posterior transforaminal interbody approach. A number of spinal implants are known in the art for these purposes. Generally, they are made from titanium, carbon or biocompatible materials and allow, either via porosity or via cavity for the ingrowth of osseous fusion.

One well described potential complication of these implanted devices arises from the possibility of their migration prior to complete consolidation of fusion. Inadvertent movement of an implanted device may lead to injury to surrounding structures such as nerves, blood vessels or viscera. Therefore, there is a need for an implant which possesses a greater movement resistance. Devices which resist migration via vertically applied members which cut into adjacent vertebrae are known to the art.

The problem posed by these devices known to the prior art lie in their cumbersome nature, difficulty in application or lack of sound biomechanical interface with surrounding anatomy. There is the need for a more elegantly designed, easily applied cage with superior biomechanical characteristics which will serve to stabilize pathologic spinal segments, resist inadvertent movement and induce spinal fusion.

SUMMARY

A spinal implant designed for application in the cervical, thoracic or lumbar aspect of the spine. The implant includes a means to secure it in place to prevent movement. In the cervical spine it may be applied via an anterior approach. In the thoracic or lumbar spine it may be applied via an anterior or lateral approach. It may be applied via the transforaminal lumbar interbody approach.

PARTS LIST

1. Cage
2. Piercing Pin
3. Pin Block
4. Locking Screw
5. Pin Block Channel
6. Insertion Pliers
7. Screw Driver
8. Vertebrate
9. Pliers Driver
10. Pliers Guide Plate
11. Eyelet
12. Pin Hole Substrate
13. Cage Guide
14. Pliers Guide
15. Cage Pin Arm
16. Cage Pin Slot
17. Pliers Handles
18. Pliers Spring
19. Pliers Driver Slot

DESCRIPTION

This invention comprises a spinal fixation and fusion device. It includes supportive elements, a hollow area intended to be filled with bone grafting material, and an anchoring device. The device is intended to fill the void created by removal of intervertebral disc material. It is intended to support the surrounding structures. One aspect of the cage is intended to resist inadvertent migration. The cage includes anterior, bilateral and posterior walls which serve to support the surrounding vertebrae. The hollow center may be filled with grafting material in order to encourage intervertebral fusion to occur. Depending upon the spinal level to be fused, and the direction of approach to the spine, the anchoring device will be intrinsic to one or more of the walls of the cage. The bone piercing anchoring device may be driven and locked into position where it may affix the surrounding vertebrae and provide the cage with resistance to movement.

The design of the cage may take various forms, depending upon to which part of the spine it will be applied, as well as the approach of application. For the anteriorly applied cervical, thoracic and lumbar device it may be comprised of an approximately quadrangular shape with four walls conforming to the shape of the cephalad and caudal vertebrae. For cages applied via the direct lateral approach in the thoracic and lumbar spine, the device may be comprised of an approximately quadrangular shape with four walls conforming to the shape of the cephalad and caudal vertebrae. For cages applied via transforaminal lumbar interbody approach, the device may be shaped approximately as an elongated kidney bean. In all cases, the cage may be hollow to allow for packing with graft material and ingrowth of bone culminating in intervertebral fusion. In all cases, the cage will be impacted into the intervertebral space according to the approach of application.

This invention provides a stabilization member integrated into one or more walls of the cage. This member may be incorporated in the wall of the cage subjected to impaction. Upon optimal placement of the cage within the intervertebral space, the stabilization member may be deployed. This will result in the member cutting into the cephalad and caudal vertebrae, thus providing the cage with resistance to movement.

The stabilization member may be advantageously deployed by easy application of a pliers-like tool specifically designed to drive the stabilization members into the surrounding bone. Deployment of the stabilization member may occur within the wall of impaction, driving pins residing within the impaction wall from a resting into a deployed position. This may result in the member cutting into the cephalad and caudal vertebrae, thus affixing the cage. The stabilization members or pins can be secured in place insertion into the cephalad and caudal vertebrae. One method to secure the pins in place after insertion into the vertebrae is to insert screws through the base of an inserted pin into a wall of the cage.

One embodiment is shown on FIGS. 1-9. The cage (1) includes one or more piercing pin(s) (2), each applied to a pin block (3) at an end opposite to the narrowed point of the pin which is designed for insertion into a vertebrae. The pin (2) with pin block (3) are located in a pin block channel (5) within a wall of the cage (1). Typically as shown on FIGS. 1-9, two pins (2) are located adjacent to each other to allow insertion of a pin into both the cephalad and caudal vertebrae. The pin block (3) is restricted to movement within the pin block channels (5) which extend from the top of a wall in the cage (1) to the bottom of a wall in the cage for insertion of the pin (2). As shown on the drawings the pin block shape is compatible with the shape of the pin block channel to ensure the pin block is only allowed movement within the pin block channel between the top and bottom of the cage.

Figure 1:
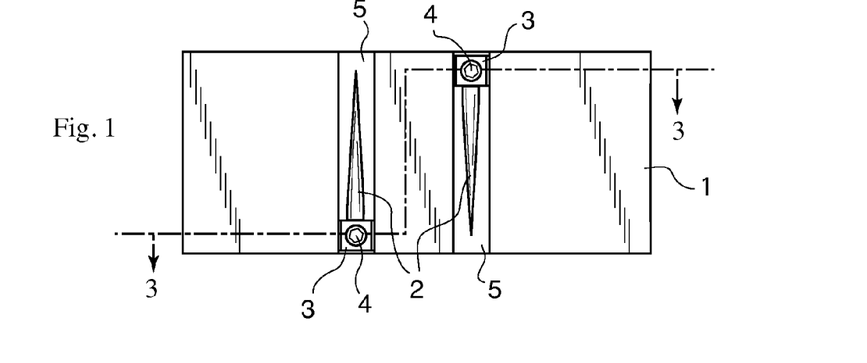
FIG. 1 is a view of one side of a cage with pins prior to insertion.
Figure 2:
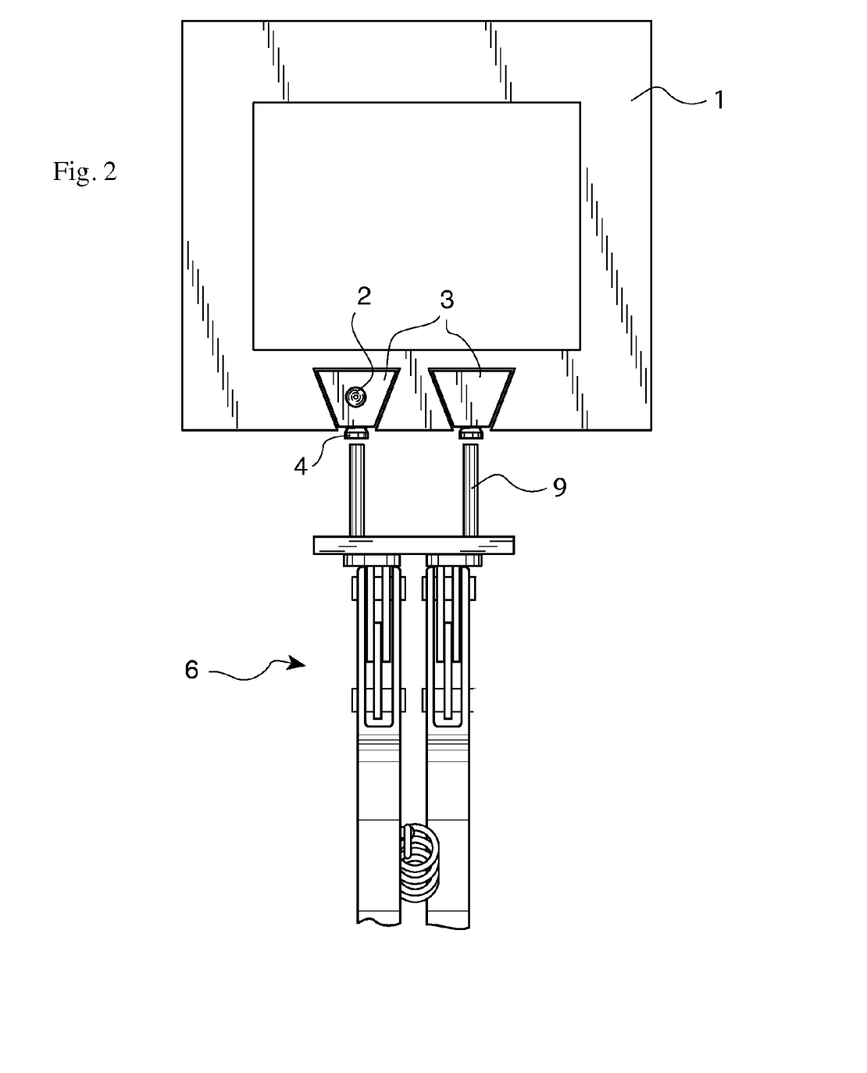
FIG. 2 is a top view of one side of a cage with pins prior to insertion.
Figure 3:
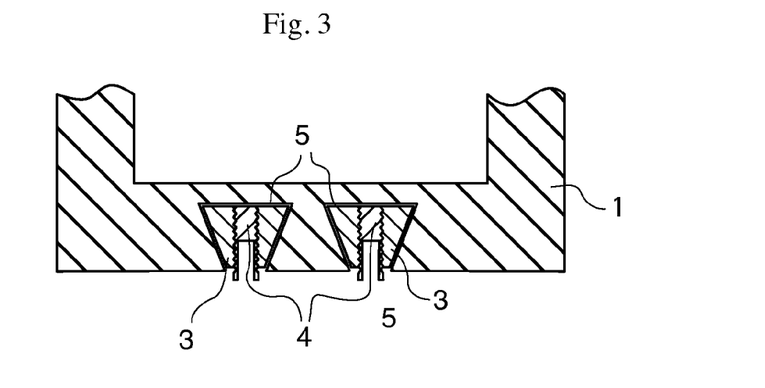
FIG. 3 is a top view of a cross section of a cage with pins prior to insertion.
Figure 4:
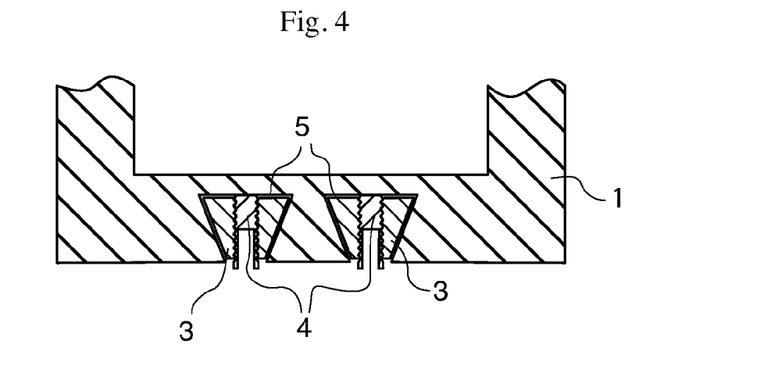
FIG. 4 is a top view of a cross section of a cage with pins inserted.
Figure 8:
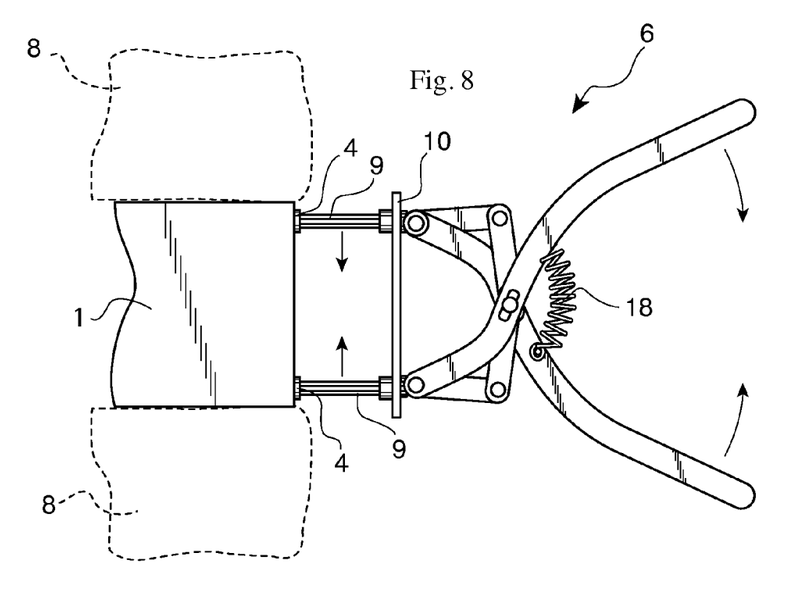
FIG. 8 is a side view of a cage positioned between two vertebrae showing cage pliers open and engaged with the pins for insertion.
Figure 9:
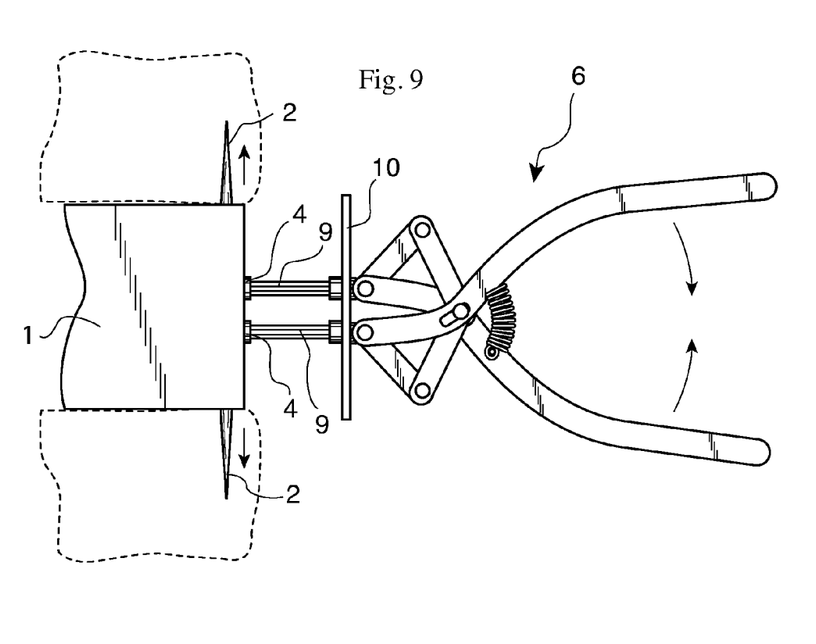
FIG. 9 is a side view of a cage positioned between two vertebrae showing cage pliers closed causing pin insertion.
Figure 10:
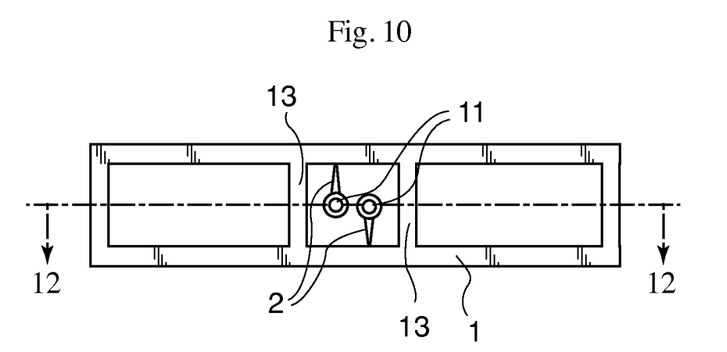
FIG. 10 is a side view of another embodiment of a cage with pins for insertion.
Figure 11:
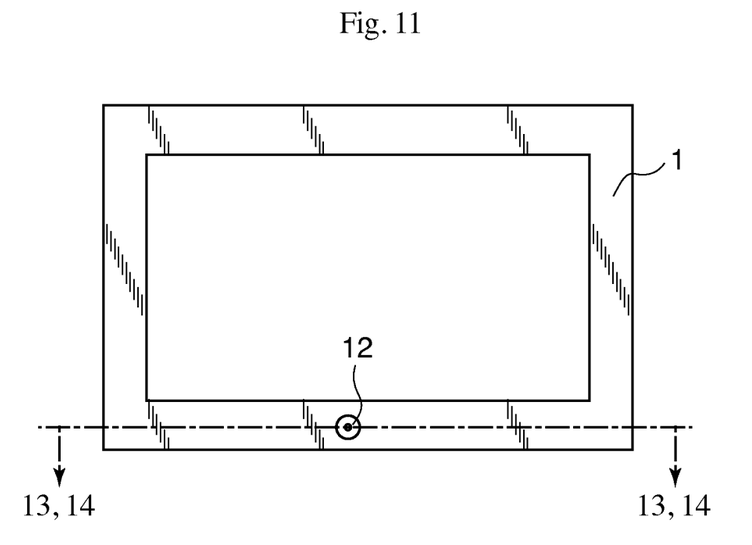
FIG. 11 is a top view of cage in FIG. 10.
Figure 12:
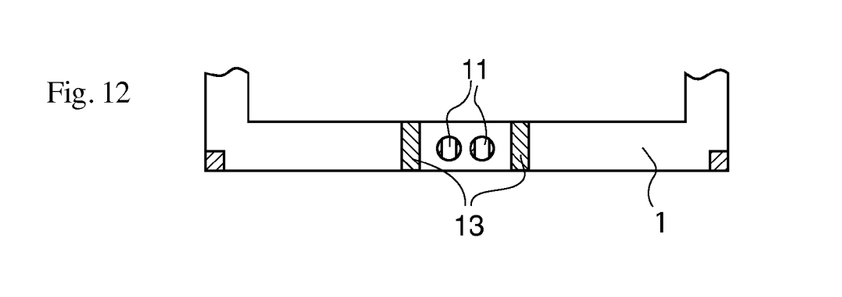
FIG. 12 is a cross section of FIG. 10.
Figure 13:
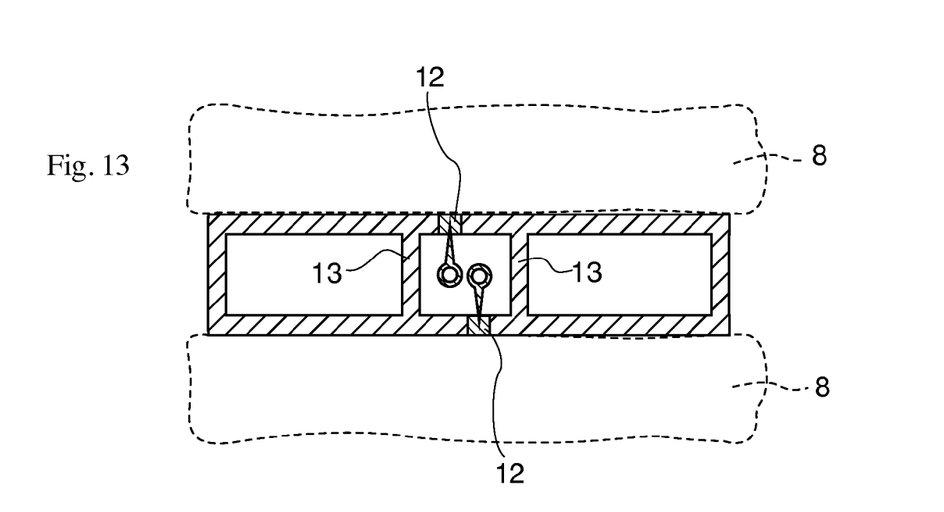
FIG. 13 is a cross section of FIG. 11 with pins prior to insertion.
Figure 14:
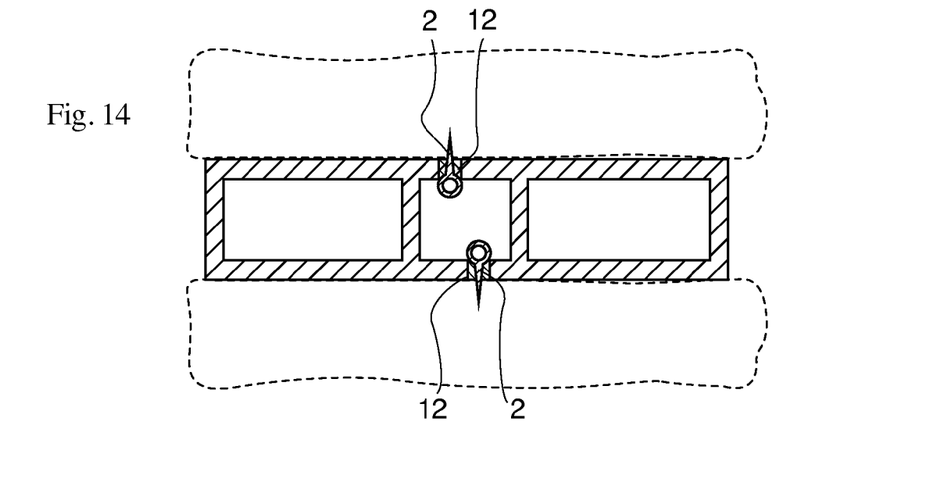
FIG. 14 is a cross section of FIG. 11 with pins shown inserted.
Figure 15:
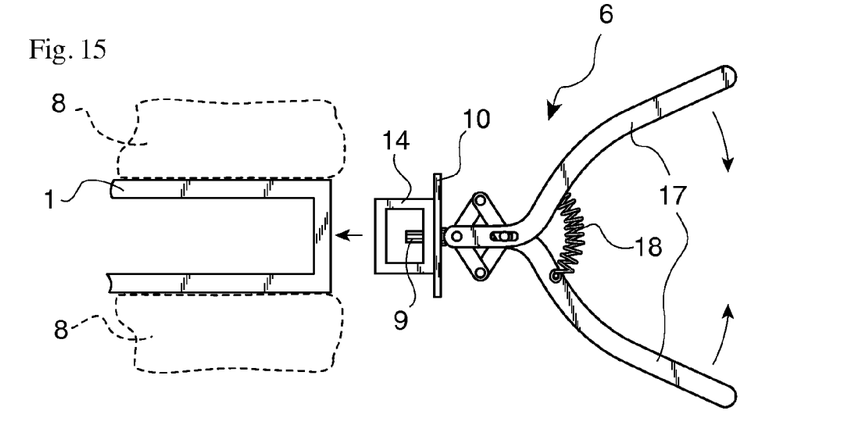
FIG. 15 is a side view of a cage positioned between two vertebrae showing cage pliers open.
Figure 16:
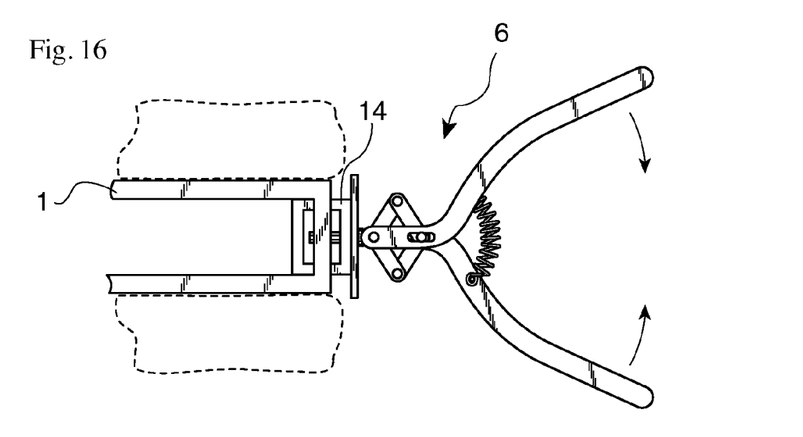
FIG. 16 is a side view of a cage positioned between two vertebrae showing cage pliers open and engaged with the pins for insertion.
Figure 17:
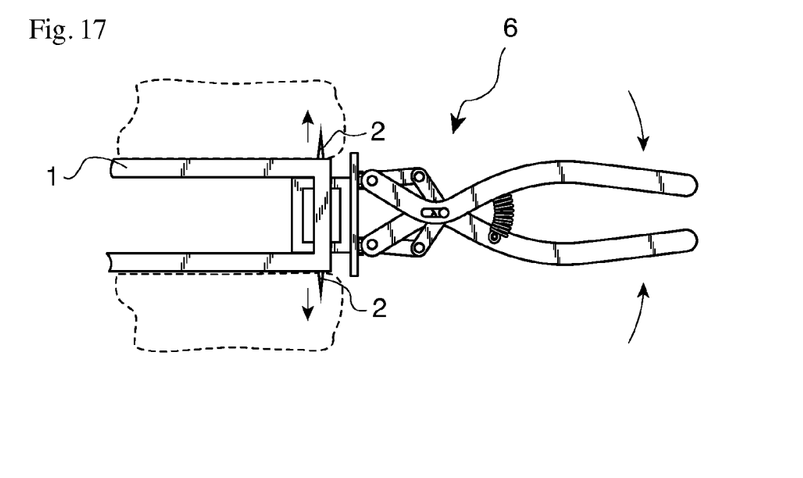
FIG. 17 is a side view of a cage positioned between two vertebrae showing cage pliers closed causing pin insertion.
Figure 18:
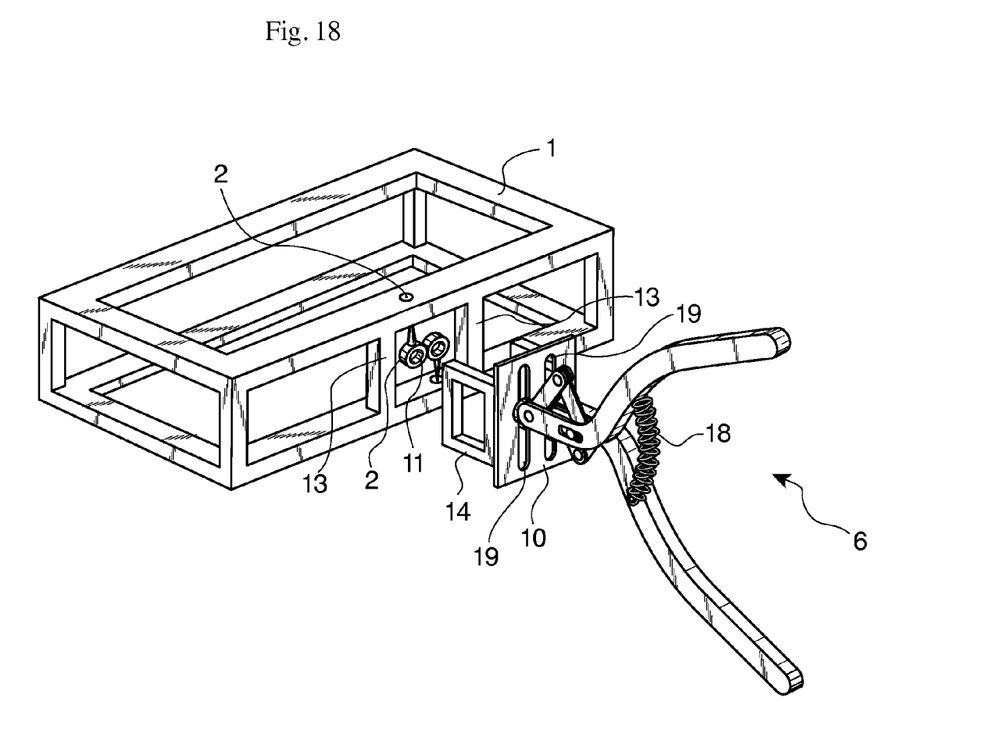
FIG. 18 is a perspective view of FIG. 10 with open pliers.
Figure 19:
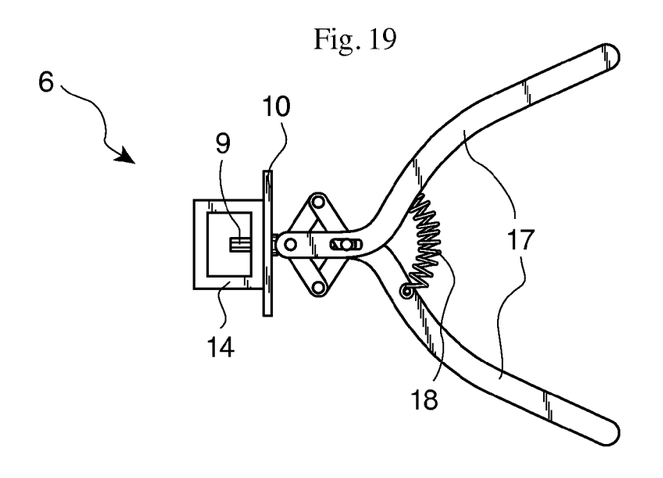
FIG. 19 is a side view of the pliers.
Figure 20:
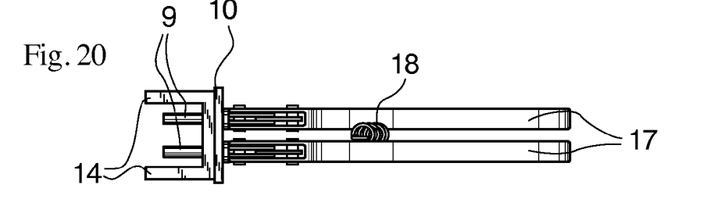
FIG. 20 is a top view of the pliers.
Figure 21:
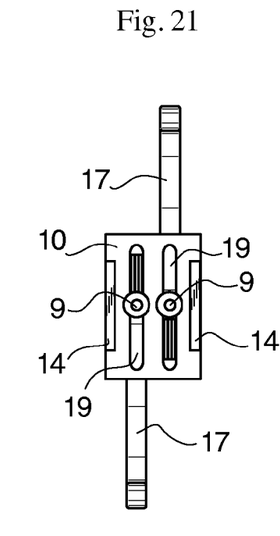
FIG. 21 is a front view of the pliers.
Figure 22:
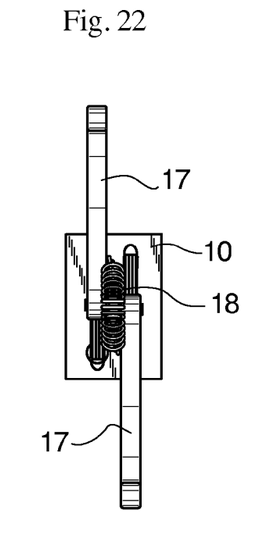
FIG. 22 is a rear view of the pliers.
Figure 23:
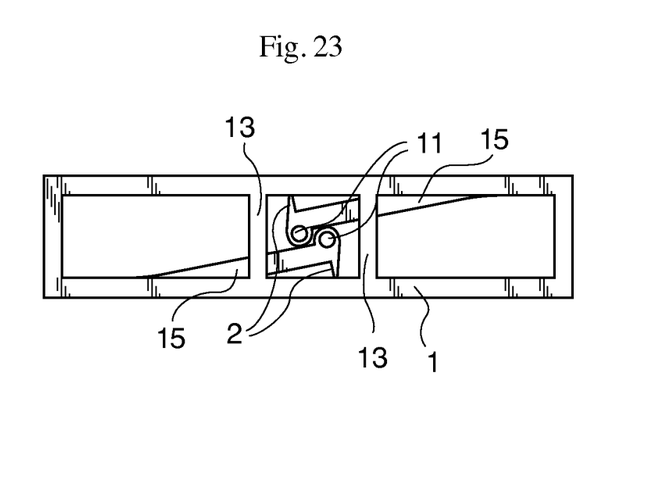
FIG. 23 is a side view of another embodiment of a cage with cage pin arrows shown prior to pin insertion.
Figure 24:
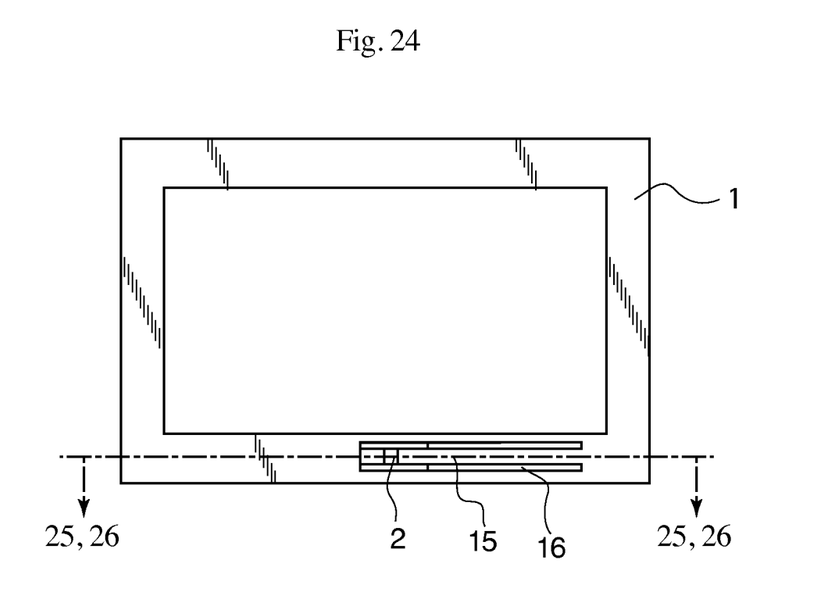
FIG. 24 is a top view of a cage with cage pin arrows shown prior to pin insertion.
Figure 25:
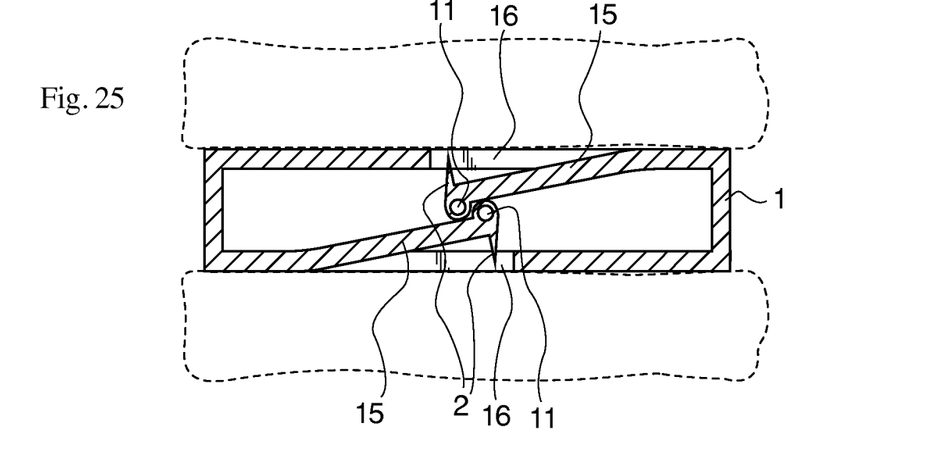
FIG. 25 is a side cross section of FIG. 23 showing pins prior to insertion.
Figure 26:
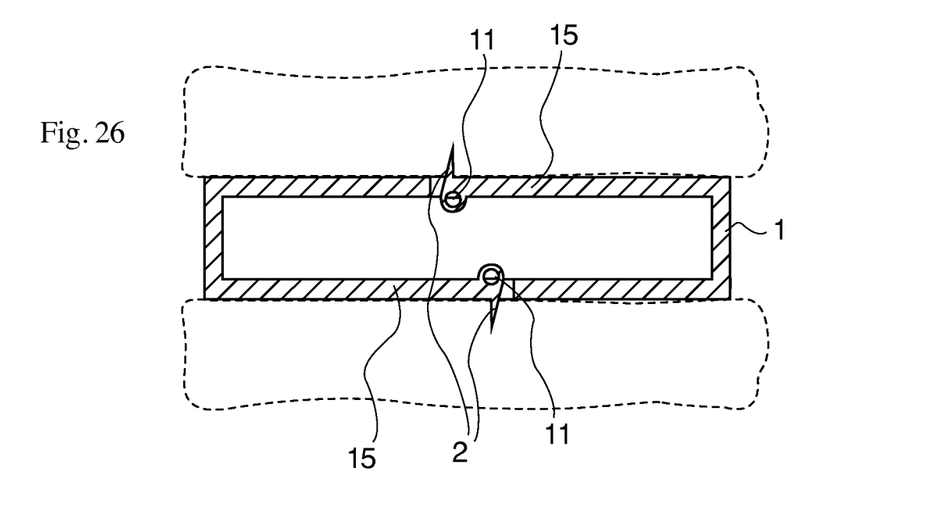
FIG. 26 is a side cross section of FIG. 23 showing pins in inserted position.

A specifically designed pliers (6) like tool allows the simultaneous deployment/insertion of pins (2) in cephalad and caudal vertebrae (FIGS. 2, 8 and 9). The insertion pliers (6) include handles (17) with a spring (18) to maintain the pliers in an open position as their default position. Pushing the handles (17) toward each other causes pliers drivers (9) to slide along a plier's driver slot within the pliers guide plate (10). The two pliers drivers (9) are moved in opposite directions in the parallel slots as the pliers are moved toward a closed position.

For insertion of the pins (2), the pliers drivers (9) are inserted into the pin blocks (3). After the insertion of the pliers drivers (9), the handles (17) are moved toward the closed position. Movement of the pliers handles (17) is stopped when the pins (2) are inserted into the vertebrae as desired. After the pins are inserted they can be secured in position.

Figure 5:
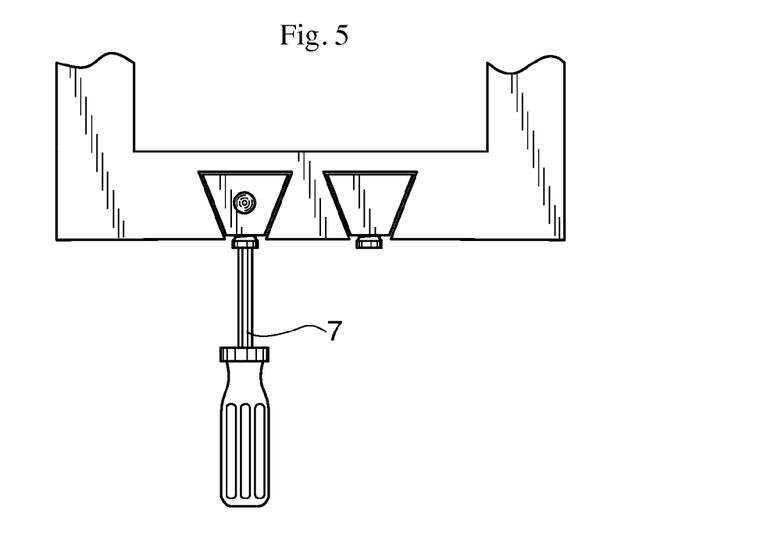
FIG. 5 is a top view of a cross section of a cage with screw driver inserted into locking screw on a pin.
Figure 6:
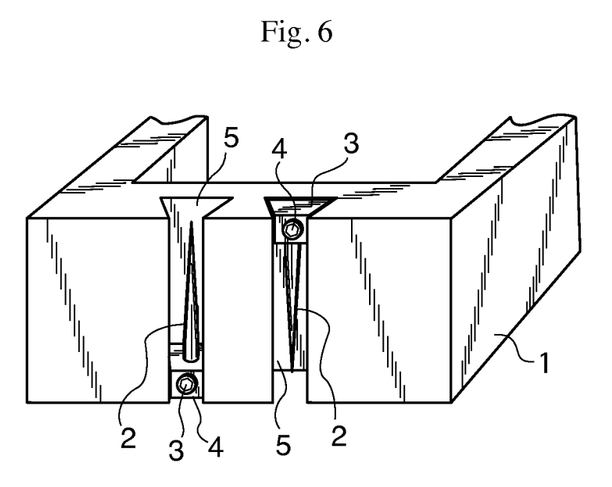
FIG. 6 is a perspective view of a cage with pins prior to insertion.
Figure 7:
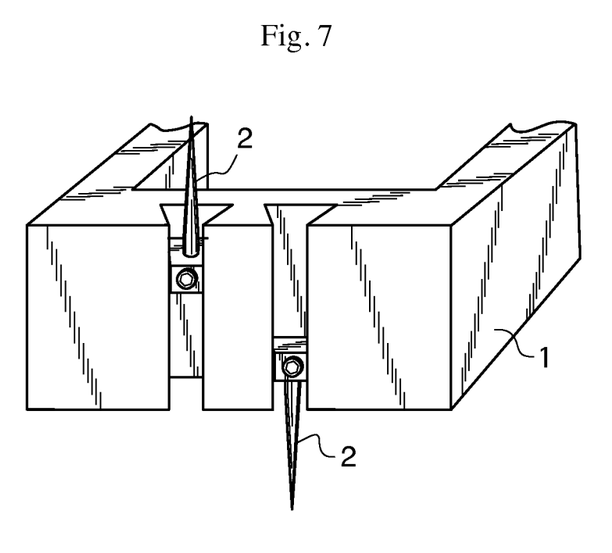
FIG. 7 is a perspective view of a cage with pins in an inserted position.

One method to do that is to insert a locking screw (4) through the pin block (3) into a wall of the cage (1) using a screw driver (7). Other methods to secure the pin block in place after pin insertion are within the skill and knowledge of those in this field.

A second embodiment is shown on FIGS. 10-18. In this embodiment the pins (2) are held in place within the wall of the cage (1) by pin hole substrate (12) in holes in the top and bottom of a wall in the cage (1). As shown on the drawings each pin has an eyelet at one end and a point at an opposite end designed for insertion into a vertebrae. The eyelet is an enclosed opening as shown on the drawings. Cage guides (13) form a typically rectangular opening in the wall of the cage (1). The specially designed pliers like tool (6) has pliers guides (14) on it designed to fit the opening in the wall of the cage (1). This allows the pliers (6) to be stabilized in the cage when it is used to drive the pins into the vertebrae. After the pliers drivers (9) are inserted in eyelets (11) on the pins (2), pliers handles (17) are moved toward each other causing insertion of the pins (20) into the cephalad and caudal vertebrae. As with the first embodiment the pin can be secured in place after insertion into a vertebrae by a locking screw or other means.

Insertion pliers (6) are shown in detail on FIGS. 19 to 22 and described above. Depending on the embodiment being used, configuration of pliers can be designed appropriately. For example, the pliers may or may not include a pliers guide (14) and its configuration can be varied as warranted.

Another embodiment is shown on FIGS. 23-27. In this embodiment one or more pin arms (15) are provided in a pin arm opening one or more walls of the cage (1) as shown on the figures. One end of the pin arm (15) is attached to the top or bottom of a wall with a pin arm opening. The other end has a pin (2) and a pin arm eyelet (11). The pin arms (15) are designed to be raised or lowered into cage pin slots (16) on the top or bottom of the pin arm opening in the associated wall in the cage (1).

Figure 27:
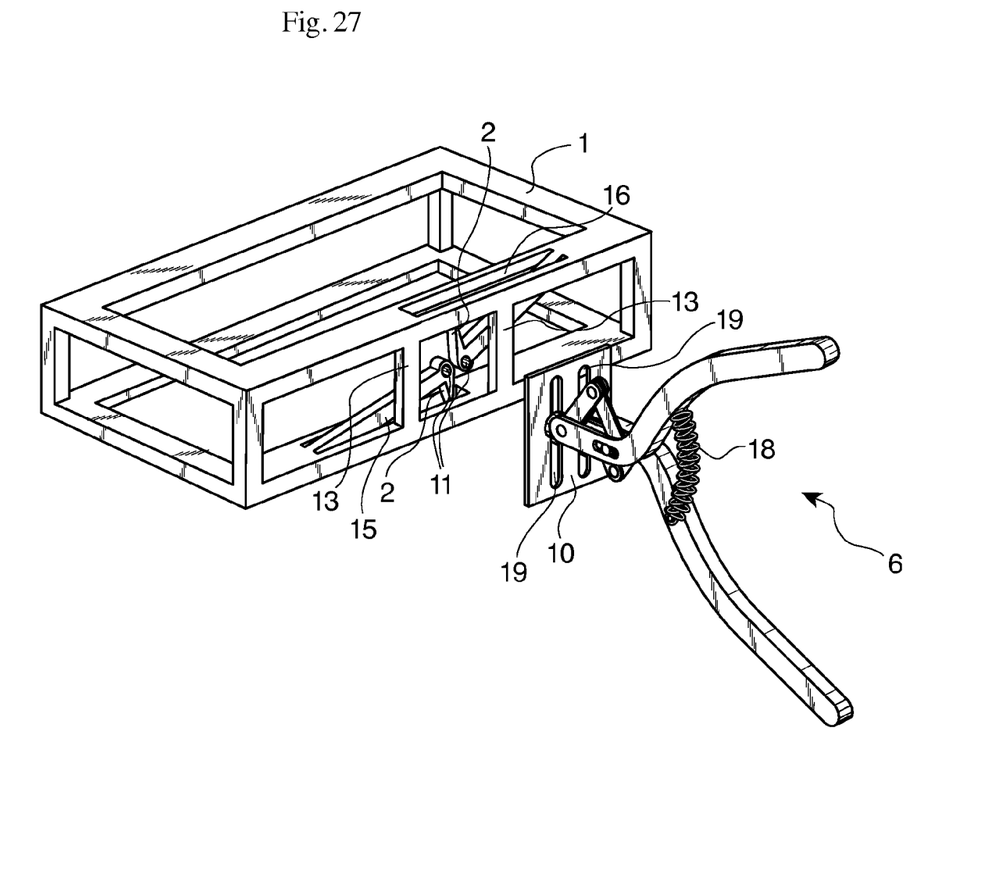
FIG. 27 is a side view of FIG. 23 and pliers in an open position.

FIG. 27 shows insertion pliers (6) designed for use with this embodiment. A pliers guide (14) allows insertion of the pliers into the cage guide in the wall of the cage (1). This aligns and stabilizes the pliers during movement of the pins (2). The pliers drivers are inserted into the eyelets of the pin arms (15). The pliers handles (17) are then moved toward the closed position causing the pin arms to be raised or lowered. When the pins (2) are inserted as desired, movement of the pliers handles (17) is stopped and the pliers drivers (9) are withdrawn. The pins can then be secured in place by a locking screw through the eyelet or other means.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

The invention claimed is:
1. A spinal fixation and fusion device comprising:
a cage configured to be positioned into an intervertebral space of a patient, the cage including:
a hollow area open through at least a top and a bottom of the cage, the hollow area comprising grafting material therein; and at least one perimeter wall surrounding the hollow area and extending between the top and the bottom of the cage, each of the at least one perimeter wall comprising:

a top surface at the top of the cage and a bottom surface at the bottom of the cage, each top surface configured to engage a cephalad vertebra and each bottom surface configured to engage a caudal vertebra;

an opening formed within at least one of the top surface and bottom surface of the at least one perimeter wall; and at least one stabilization member integral with the at least one perimeter wall, the stabilization member positioned within the at least one opening in at least one of the top surface or the bottom surface of the at least one perimeter wall, wherein the cage has a vertical axis extending between the top surface and the bottom surface and a longitudinal axis extending along the at least one perimeter wall, perpendicular to the vertical axis;

wherein the stabilization member is at least one pin at a first end of a pin arm with a second opposite end of the pin arm attached to either the top surface or the bottom surface of the at least one of the perimeter wall, wherein the stabilization member is designed to be pivoted relative to the top surface or the bottom surface between a raised position and a lowered position, the pin configured to pass through a cage pin slot formed in the top surface or the bottom surface, the cage pin slot being open into the opening such that:

when in the lowered position, the stabilization member resides entirely within the opening and the pin arm extends at a non-parallel angle relative to the longitudinal axis, and when in the raised position, the pin extends upwardly or downwardly past the top surface or bottom surface for insertion into at least one of the cephalad vertebra or the caudal vertebra, and the pin arm remains within the opening and extends parallel to the longitudinal axis, and wherein the cage pin slot is sized to allow only a portion of the pin which is designed to be inserted into the cephalad vertebra or the caudal vertebra to extend beyond the top surface or the bottom surface of the cage when in the raised position, with the remainder of the pin remaining within in the opening in the at least one perimeter wall.

2. A spinal fixation and fusion device according to claim 1 wherein there are 2 pins with pin arms with one pin pointed toward a cage pin slot in the top wall; with a second pin pointed toward a cage pin slot in the bottom wall; and further comprising an eyelet on each pin arm.

3. A spinal fixation and fusion device according to claim 2 further comprising a cage guide opening in the wall of the cage in which the pins are located.

4. A spinal fixation and fusion system comprising:

the spinal fixation and fusion device of claim 3; and a pliers configured to control movement of the pins between the lowered position and the raised position, the pliers comprising:

two handles;

a spring positioned between the two handles and attached thereto;

two pliers drivers positioned at distal ends of the two handles, with each pliers driver designed for insertion into a pin block positioned on the at least one stabilization member; and a pliers guide plate located between an end of the pliers drivers and the spring between the two handles, wherein the pliers guide plate is designed to be secured in the cage guide opening in the at least one perimeter wall of the cage during operation of the pliers to permit insertion of the pins into one of the caudal vertebra or the cephalad vertebra, and wherein the pliers are designed such that movement of the pliers handles toward each other causes the pliers drivers to move in opposite directions.

* * * * *